(12) United States Patent
Gull et al.

(10) Patent No.: US 7,399,768 B2
(45) Date of Patent: Jul. 15, 2008

(54) QUINOLINE DERIVATIVES

(75) Inventors: Peter Gull, Pfeffingen (CH); Esteban Pombo Villar, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/506,232

(22) PCT Filed: Mar. 6, 2003

(86) PCT No.: PCT/EP03/02321

§ 371 (c)(1),
(2), (4) Date: Apr. 18, 2005

(87) PCT Pub. No.: WO03/074511

PCT Pub. Date: Sep. 12, 2003

(65) Prior Publication Data

US 2005/0234085 A1     Oct. 20, 2005

(30) Foreign Application Priority Data

Mar. 7, 2002    (EP) ................................. 02005115

Mar. 7, 2002    (EP) ................................. 02005117

(51) Int. Cl.
*A61K 31/473*    (2006.01)
*C07D 221/06*    (2006.01)

(52) U.S. Cl. ........................................ 514/290; 546/79
(58) Field of Classification Search .................. 546/79; 514/290

See application file for complete search history.

(56) References Cited

U.S. PATENT DOCUMENTS 6,057,334 A * 5/2000 Gull et al. ................... 514/290

FOREIGN PATENT DOCUMENTS

WO    WO 98 01444    1/1998

* cited by examiner

*Primary Examiner*—Rita J Desai
(74) *Attorney, Agent, or Firm*—Cozette M. McAvoy; John Alexander

(57) ABSTRACT

The present invention relates to novel benzo [g] quinoline derivatives, their preparation, their use as pharmaceuticals for use in the treatment of glaucoma and myopia.

3 Claims, No Drawings

QUINOLINE DERIVATIVES

The present invention relates to novel benzo [g] quinoline derivatives, their preparation, their use as pharmaceuticals and pharmaceutical compositions containing them.

The present present invention pertains to a compound selected from the group consisting of compound of formula Ia,

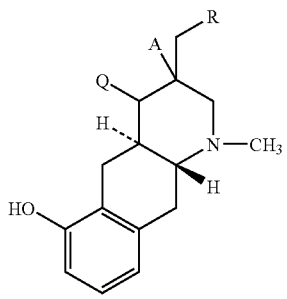

Ia

Wherein A and Q are each H or form together an additional bond, and wherein the asymmetric center in position 3 may be racemic, or in form of an optically active form, and wherein R is of formula Ib or Ic,

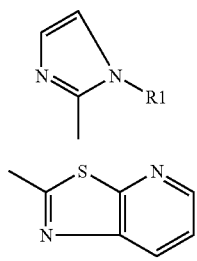

Ib

Ic and wherein R1 is alkyl, in free base or acid addition salt form.

In a preferred aspect A and Q are each H. In a further preferred aspect A and Q form together an additional bond.

The substituent CH2—R in position 3 of formula Ia is preferably in configuration 3R, provided A and Q are each H.

R1 is preferably selected from alkyl having from 1 to 4 carbon atoms. Accordingly, as used herein, alkyl is especially $C_1$-$C_4$-alkyl, e.g. n-butyl, sec-butyl, tert-butyl, n-propyl, iso-propyl, or especially methyl or also ethyl.

In a more preferred aspect R1 is $C_1$-alkyl e.g. methyl.

More particularly the present invention pertains to a compound selected from the group consisting of compound of formula I and compound of formula II,

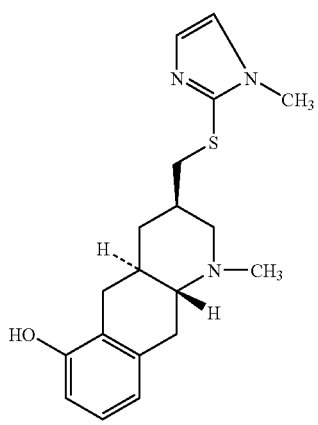

I

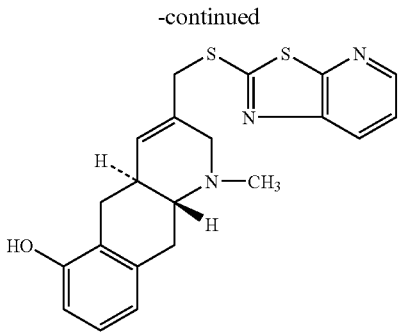

II wherein the CH2—S-imidazol substituent in formula I presents the configuration 3R, in free base or acid addition salt form.

An even more preferred aspect of the present invention is a compound of formula I as defined above. Also highly preferred is a compound of formula II as defined above.

Acid addition salts may be produced from the free bases in known manner, and vice versa. Suitable acid addition salts for use in accordance with the present invention include for example the hydrochloride.

The compounds of formula Ia, I and II and their physiologically acceptable acid addition salts, referred to hereinafter as compounds of the invention, exhibit valuable pharmacological properties in animal tests and are therefore useful as pharmaceuticals.

Prior Art:

The compounds of the present invention exhibit favorable pharmacological properties vis-à-vis the closest prior art, e.g. EP 912'553.

DETAILED DESCRIPTION OF THE PRESENT INVENTION

In particular, the compounds according to the invention produce a decrease on the intraocular pressure (IOP) in rabbits, at concentrations of 10 to 100 μM. Male rabbits of ca. 2.5 kg are fixed in cages leaving their heads free. The solutions with the compound to be tested are applied to the right eye and the placebo solutions to the left eye (2 drops each, i.e. ca. 40 μl). The eyes are firstly anaesthetized with a solution containing Novesine (0.4%) and Fluorescein (0.05%) and the ocular pressure is determined at various intervals after administration (10, 20, 30, 60, 90, 120, 180 and 240 minutes), whereby an applanation tonometer according to Goldberg is used.

Surprisingly, the compounds according to the invention exhibit a strong IOP-lowering efficacy, an excellent tolerability, and a long duration of action, and are therefore in particular useful in the treatment of glaucoma and myopia. In a preferred aspect it refers to the treatment of glaucoma.

For the above mentioned indication, the appropriate dosage will of course vary depending upon, for example, the compound employed, the host, the mode of administration and the severity of the condition being treated. However, in general, satisfactory results in animals are indicated to be obtained at a daily dosage of from about 0.1 to about 10 mg/kg animal body weight. In larger mammals, for example humans, an indicated daily dosage is in the range from about 5 to about 200 mg, preferably about 10 to about 100 mg of the compound conveniently administered in divided doses up to 4 times a day or in sustained release form.

The compounds of the invention may be administered in free form or in pharmaceutically acceptable salt form. Such salts may be prepared in conventional manner and exhibit the same order of activity as the free compounds.

Accordingly the present invention provides a compound of the invention for use as a pharmaceutical, e.g. in the treatment of glaucoma and myopia.

The present invention furthermore provides a pharmaceutical composition comprising a compound of the invention in association with at least one pharmaceutically acceptable diluent or carrier. Such compositions may be formulated in conventional manner. Unit dosage forms contain, for example, from about 0.25 to about 50 mg of a compound according to the invention.

Compounds according to the invention may be administered by any conventional route, for example parenterally e.g. in form of injectable solutions or suspensions, or enterally, preferably orally, e.g. in the form of tablets or capsules.

More preferably, they are applied topically to the eye in ca. 0.002 to 0.02% ophthalmological solutions.

The ophthalmic vehicle is such that the compound is maintained in contact with the ocular surface for a sufficient time period to allow the compound to penetrate the corneal and internal regions of the eye.

The pharmaceutically acceptable ophthalmic vehicle may be e.g. an ointment, vegetable oil, or an encapsulating material.

In accordance with the foregoing, the present invention also provides a compound of the invention for use as a pharmaceutical in the treatment of glaucoma and myopia.

Moreover the present invention provides the use of a compound of the invention, for the manufacture of a medicament for the treatment of glaucoma and myopia.

In still a further aspect the present invention provides a method for the treatment of glaucoma and myopia in a subject in need of such treatment, which comprises administering to such subject a therapeutically effective amount of a compound of the invention.

EXAMPLE 1

[3R,4aR,10aR]-1-methyl-3β-hydroxymethyl-6-methoxy-1,2,3,4,4aα,5,10, 10aβ-octahydrobenzo[q]quinoline To a solution of 5.78 g (20 mM) [3R,4aR,10aR]-1-methyl-3β-methoxycarbonyl-6-methoxy-1,2,3,4,4aα,5,10,10aβ-octahydrobenzo[g]quinoline in 100 ml toluene, a solution of 12 ml SDBA (sodium dihydro-bis-(2-mthoxyethoxy) aluminate) (70% in toluene, 42 mM) are added in drops under argon at room temperature within one hour. Then 10 ml NaOH (30%) are added in drops to the ice cooled reaction mixture. The precipitated crystals are filtered off, washed with water and toluene and dried. The resulting title compound has a m.p. of 148°; $[\alpha]^{20}_D = -120°$ (c=0.425 in ethanol).

EXAMPLE 2

[3R,4aR,10aR]-1-methyl-3β-mesyloxymethyl-6-methoxy-1,2,3,4,4aα,5,10, 10aβ-octahydrobenzo[g]quinoline 12 ml (153 mM) methanesulfochloride are added in drops to a solution of 20 g (76.5 mM) of the compound obtained under example 1 in 150 ml pyridine at room temperature. The temperature is kept below 45° by ice cooling. After stirring for 2 hours at room temperature, the solution is adjusted to pH 7-8 with saturated $KHCO_3$ solution at 0° and extracted with ethylacetate. After drying over $Na_2SO_4$, filtering and concentrating by evaporation, the title compound is obtained as beige crystals and directly used for the next step.

EXAMPLE 3

A solution of 2 g (5.9 mmol) of the mesylate, as obtained in example 2, and 1 g (8.8 mM) 1-methyl-2-mercapto-imidazole in 30 ml dimethylformamide are mixed with 2 ml 10 N NaOH and stirred at 60° C. for 3 hours. The resulting suspension is concentrated by evaporation under vacuum and is then extracted with ethylacetate/isopropanol (9:1). After drying over Na2SO4, filtration, and removing of the solvent under vacuum, the methyl ether of the compound of formula I is obtained, which is then directly used for the next step.

EXAMPLE 4

Compound of Formula I

To a solution of 1.76 g (5 mmol) of the compound obtained in example 1 in 10 ml methylenechloride, 25 ml boron tribromide (1 molar in methylenechloride) are slowly added in drops at a temperature of −50° C. The suspension is stirred for 3 hours at room temperature, neutralized with aqueous ammonia and extracted with ethylacetate/isopropanol (9:1). The extract is dried over sodium sulfate, filtered and the solvent removed under vacuum. An excess amount of hydrochloric acid in methanol is added, until pH=1 is reached. The solvent is then gradually removed until crystallization occurs. The hydrochloride is re-crystallized from methanol/ethanol (1:1), m.p. 272-274° C. $\alpha_D^{20} = -38°$ (c=0.375 in ethanol/water). $C_{19}H_{25}N_3OS$ (2 HCl), MW=416.4.

EXAMPLE 5

To a solution of 4 g (15.4 mM) of 1,2,4aS-trans-5,10,10a-hexahydro-6-methoxy-1-methyl-3-hydroxymethyl-benzo[g]quinoline (see Registry No. 201869-32-1, Chem. Abstr.) in 40 ml toluene, 1.3 ml (17.9 mM) thionylchloride are slowly added dropwise at a temperature of 0° C. The suspension is stirred for 12 hours at room temperature. The resulting chloride crystallizes spontaneously. After filtration and washing with toluene, the product is directly used in the next step.

EXAMPLE 6

To a solution of 4 g (17.6 mM) of the chloride as obtained in example 5 in 100 ml dichloromethane, 50.5 ml 1 molar boron tribromide in dichloromethane are slowly added at −70° C. The suspension is stirred for 3 hours at room temperature, neutralized with NaHCO3 and extracted with ethylacetate/isopropanol (9:1). After drying over Na2SO4, filtering and concentration by evaporation, the corresponding 6-hydroxy-benzo[g]quinoline derivative is directly used in the next step.

EXAMPLE 7

Compound of Formula II

A solution of 930 mg (3.5 mM) of the 6-hydroxy-benzo[g]quinoline derivative of example 6 and 705 mg (4.2 mM) thiazolo[4,5-b]pyridine-2-thiol in 30 ml dimethylformamide is mixed with 10N NaOH and stirred at room temperature for 1 hour. The resulting suspension is concentrated by evaporation under vacuum and is then extracted with ethylacetate/isopropanol (9:1). After drying over Na2SO4, filtration, and removing of the solvent under vacuum, the resulting residue is chromatographed over silica using dichloromethane/ethylacetate/methanol in a ratio of 40:55:5. The purified material is then converted into the hydrochloride by adding HCl in ethanol and subsequent evaporation. Re-crystallization from methanol/ethanol furnished the compound of formula II as hydrochloride, with a m.p. of 240° C. (decomp.), $\alpha_D^{20}=$ −101° (c=0.405 in ethanol/water). $C_{21}H_{21}N_3OS_2$ (HCl), MW=432.01.

The invention claimed is:

1. A compound, in free base or acid addition salt form, according to formula I

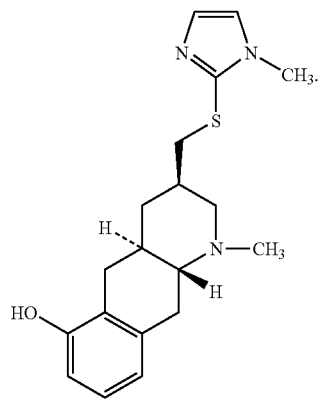

I

2. A method for the inhibition of intraocular pressure in a subject in need of such treatment, which comprises administering to such subject a therapeutically effective amount of a compound according to claim 1 in free base or pharmaceutically acceptable acid addition salt form.

3. A pharmaceutical composition comprising a compound of claim 1 and at least one pharmaceutically acceptable diluent or carrier.

* * * * *